United States Patent
Boss et al.

(10) Patent No.: US 11,299,174 B2
(45) Date of Patent: Apr. 12, 2022

(54) DUAL-TEST OPERATOR ASSESSMENT

(71) Applicant: KYNDRYL, INC., New York, NY (US)

(72) Inventors: Gregory J. Boss, Saginaw, MI (US);
Michael Bender, Rye Brook, NY (US);
Jeremy R. Fox, Georgetown, TX (US);
Manjari Roy, Danbury, CT (US)

(73) Assignee: KYNDRYL, INC., New York, NY (US)

( * ) Notice: Subject to any disclaimer, the term of this patent is extended or adjusted under 35 U.S.C. 154(b) by 818 days.

(21) Appl. No.: 16/193,079

(22) Filed: Nov. 16, 2018

(65) Prior Publication Data

US 2020/0156654 A1    May 21, 2020

(51) Int. Cl.
*B60R 1/00* (2022.01)
*B60W 50/14* (2020.01)
(Continued)

(52) U.S. Cl.
CPC .............. *B60W 50/14* (2013.01); *A61B 5/12* (2013.01); *A61B 5/162* (2013.01); *A61B 5/18* (2013.01);
(Continued)

(58) Field of Classification Search
CPC .. B60W 50/14; B60W 30/09; B60W 2540/26; A61B 5/12; A61B 5/162;
(Continued)

(56) References Cited

U.S. PATENT DOCUMENTS

| 5,729,619 A | 3/1998 | Puma |
| 6,243,015 B1 * | 6/2001 | Yeo .................. G08B 21/06 340/575 |

(Continued)

FOREIGN PATENT DOCUMENTS

GB    2465439 A    4/2009

OTHER PUBLICATIONS

A. Liu (2011) "Modeling Differences in Behavior Within and Between Drivers." In: Cacciabue P., Hjalmdahl M., Luedtke A., Riccioli C. (eds) Human Modelling in Assisted Transportation. Springer, Milano, entire document.

(Continued)

*Primary Examiner* — Munear T Akki
(74) *Attorney, Agent, or Firm* — Ken Han; Andrew M. Calderon; Roberts Calderon Safran & Cole P.C.

(57) ABSTRACT

In response to determining that performance data of device operation by an operating user meets a safety requirement, embodiments determine a degree of deviation of a performance data value from a baseline pattern of good performance values defined for the user; in response to determining that the degree of deviation of the operating data value meets a cognitive assessment threshold, administer a cognitive aptitude test challenge to the user selected from baseline aptitude profile data of challenges previously responded to by the user; and execute a corrective action that reduces a risk of loss in response to determining that a degree of deviation of a value of a response provided by the user to the cognitive test challenge from a performance metric value of the baseline aptitude profile data meets a threshold cognitive assessment threshold.

20 Claims, 5 Drawing Sheets

(51) Int. Cl.
*B60Q 9/00* (2006.01)
*G05D 1/00* (2006.01)
*A61B 5/12* (2006.01)
*A61B 5/16* (2006.01)
*A61B 5/18* (2006.01)
*B60W 30/09* (2012.01)
*G06N 20/00* (2019.01)

(52) U.S. Cl.
CPC .............. *B60Q 9/00* (2013.01); *B60W 30/09* (2013.01); *G05D 1/0061* (2013.01); *G06N 20/00* (2019.01); *B60W 2540/26* (2013.01)

(58) Field of Classification Search
CPC ......... A61B 5/18; A61B 5/165; A61B 5/4845; A61B 5/1118; A61B 5/0205; A61B 5/145; A61B 5/6893; A61B 5/6898; A61B 5/168; A61B 5/4803; B60Q 9/00; G05D 1/0061; G06N 20/00; G06V 20/597; G07C 5/008; G07C 5/0841
See application file for complete search history.

(56) References Cited

U.S. PATENT DOCUMENTS

| | | | |
|---|---|---|---|
| 7,027,621 B1 | 4/2006 | Prokoski | |
| 7,042,345 B2 | 5/2006 | Ellis | |
| 8,063,786 B2* | 11/2011 | Manotas, Jr. | A61B 5/18 |
| | | | 340/576 |
| 8,725,311 B1 | 5/2014 | Breed | |
| 9,290,174 B1 | 3/2016 | Zagorski | |
| 9,377,852 B1* | 6/2016 | Shapiro | G06F 3/167 |
| 9,884,628 B1 | 2/2018 | Grant | |
| 9,956,963 B2 | 5/2018 | Vijaya Kumar | |
| 9,988,055 B1* | 6/2018 | O'Flaherty | G08B 21/06 |
| 2007/0055164 A1* | 3/2007 | Huang | A61B 5/6887 |
| | | | 600/508 |
| 2007/0257804 A1* | 11/2007 | Gunderson | G06Q 40/08 |
| | | | 340/576 |
| 2009/0156904 A1* | 6/2009 | Shen | A61B 5/318 |
| | | | 600/300 |
| 2009/0273487 A1* | 11/2009 | Ferro | B64C 1/1469 |
| | | | 340/963 |
| 2012/0150387 A1* | 6/2012 | Watson | A61B 5/18 |
| | | | 701/36 |
| 2013/0070043 A1* | 3/2013 | Geva | B60K 28/066 |
| | | | 348/14.02 |
| 2013/0335213 A1 | 12/2013 | Sherony | |
| 2014/0167967 A1* | 6/2014 | He | B60W 50/14 |
| | | | 340/576 |
| 2014/0240132 A1 | 8/2014 | Bychkov | |
| 2015/0066284 A1 | 3/2015 | Yopp | |
| 2015/0258892 A1* | 9/2015 | Wu | G06K 9/0061 |
| | | | 340/576 |
| 2016/0090097 A1* | 3/2016 | Grube | A61B 5/18 |
| | | | 340/576 |
| 2017/0367590 A1* | 12/2017 | Sebe | A61B 5/0077 |
| 2018/0025636 A1 | 1/2018 | Boykin | |
| 2018/0162307 A1 | 6/2018 | Boss | |
| 2020/0163560 A1* | 5/2020 | Chang | G06T 7/74 |
| 2020/0214614 A1* | 7/2020 | Rundo | A61B 5/02405 |

OTHER PUBLICATIONS

Anonymous, "Using vehicle driving patterns to provide early warning of cognitive impairment." IP.com Disclosure No. IPCOM000223158D, Publication Date: Nov. 5, 2012, entire document.

Kumar et al., Drunk-Driver Detection and Alert System (DDDAS) for Smart Vehicles, American Journal of Traffic and Transportation Engineering, 2017, entire document, vol. 2, No. 4, Science Publishing Group, http://www.sciencepublishinggroup.com/j/ajtte.

Nissan, "Drunk-Driving Prevention Concept Car," Nissan Future Technology, p. 1-2, Nissan Motor Corporation, https://www.nissan-global.com/EN/TECHNOLOGY/OVERVIEW/dpcc.html, Accessed on Apr. 24, 2018, entire document.

Peter Mell et al., The NIST Definition of Cloud Computing, National Institute of Standards and Technology, Publication 800-145, 2011, entire document.

\* cited by examiner

DUAL-TEST OPERATOR ASSESSMENT

TECHNICAL FIELD

The present invention relates generally to a method, system, and computer program product for performance assessment. More particularly, the present invention relates to a method, system, and computer program product for assessing performance qualities associated with device operation.

BACKGROUND

Injuries and property damage result from device accidents caused by inattentive or impaired operators, including vehicle operators cognitively distracted by processing competing information, such as messaging from smart phones, or cognitively impaired by fatigue, illness or consumption of intoxicants.

Some accidents may be prevented by advanced safety monitoring systems that monitor conditions exterior to a device for movements that may cause an accident, including violations of permissible movements, such as outside of a designated path or lane of travel, or travelling at rates of speed that are inappropriate for safe control (including as a function of speed ratings for a designated lane, or for the device equipment. Advanced safety monitoring systems may also monitor for possible impacts with objects located within a current trajectory of movement.

Safety monitoring systems may provide warnings to operators to correct manual control of movements to mitigate the risk of accident, including directions to change path or speed or movement, to redirect motion of the device back into an approved lane or path at a safe speed, and to prevent collision with other objects. Some systems may automatically control the motion of the device, such as by stopping or slowing movement through direct application of braking systems, or directly providing inputs to steering systems to revise a current or projected path of motion.

SUMMARY

In one aspect of the present invention, a computerized method includes, in response to determining that performance data of operation of a device by an operating user meets a safety requirement, determining a degree of deviation of a value of the performance data from a baseline pattern of good performance values defined for the user; in response to determining that the degree of deviation of the operating data value meets a cognitive assessment threshold, administering a cognitive aptitude test to the user that includes a cognitive test challenge that is selected from baseline aptitude profile data of challenges previously responded to by the user; and, in response to determining that a degree of deviation of a value of a response provided by the user to the cognitive test challenge from a performance metric value of the baseline aptitude profile data meets a threshold cognitive assessment threshold, executing a corrective action that reduces a risk of loss from impaired cognitive performance in operation of the device by the user.

In another aspect, a system has a hardware processor in circuit communication with a computer readable memory and a computer-readable storage medium having program instructions stored thereon. The processor executes the program instructions stored on the computer-readable storage medium via the computer readable memory and is thereby configured to, in response to determining that performance data of operation of a device by an operating user meets a safety requirement, determine a degree of deviation of a value of the performance data from a baseline pattern of good performance values defined for the user; in response to determining that the degree of deviation of the operating data value meets a cognitive assessment threshold, administer a cognitive aptitude test to the user that includes a cognitive test challenge that is selected from baseline aptitude profile data of challenges previously responded to by the user; and, in response to determining that a degree of deviation of a value of a response provided by the user to the cognitive test challenge from a performance metric value of the baseline aptitude profile data meets a threshold cognitive assessment threshold, execute a corrective action that reduces a risk of loss from impaired cognitive performance in operation of the device by the user.

In another aspect, a computer program product includes instructions for execution which cause a processor to, in response to determining that performance data of operation of a device by an operating user meets a safety requirement, determine a degree of deviation of a value of the performance data from a baseline pattern of good performance values defined for the user; in response to determining that the degree of deviation of the operating data value meets a cognitive assessment threshold, administer a cognitive aptitude test to the user that includes a cognitive test challenge that is selected from baseline aptitude profile data of challenges previously responded to by the user; and, in response to determining that a degree of deviation of a value of a response provided by the user to the cognitive test challenge from a performance metric value of the baseline aptitude profile data meets a threshold cognitive assessment threshold, execute a corrective action that reduces a risk of loss from impaired cognitive performance in operation of the device by the user.

BRIEF DESCRIPTION OF THE DRAWINGS

These and other features of embodiments of the present invention will be more readily understood from the following detailed description of the various aspects of the invention taken in conjunction with the accompanying drawings in which.

DETAILED DESCRIPTION

Figure 1:
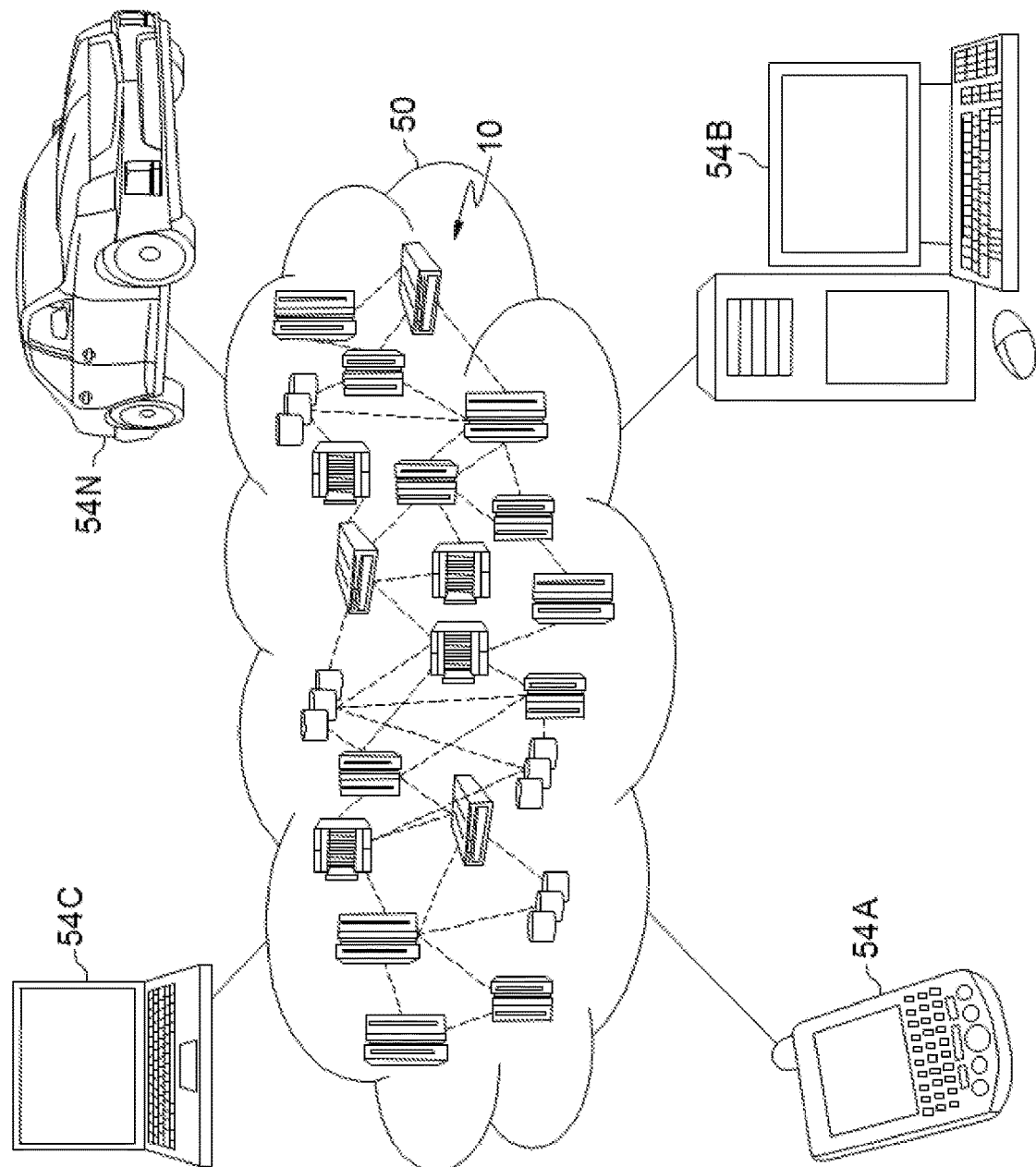
FIG. 1 depicts a cloud computing environment according to an embodiment of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and be rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
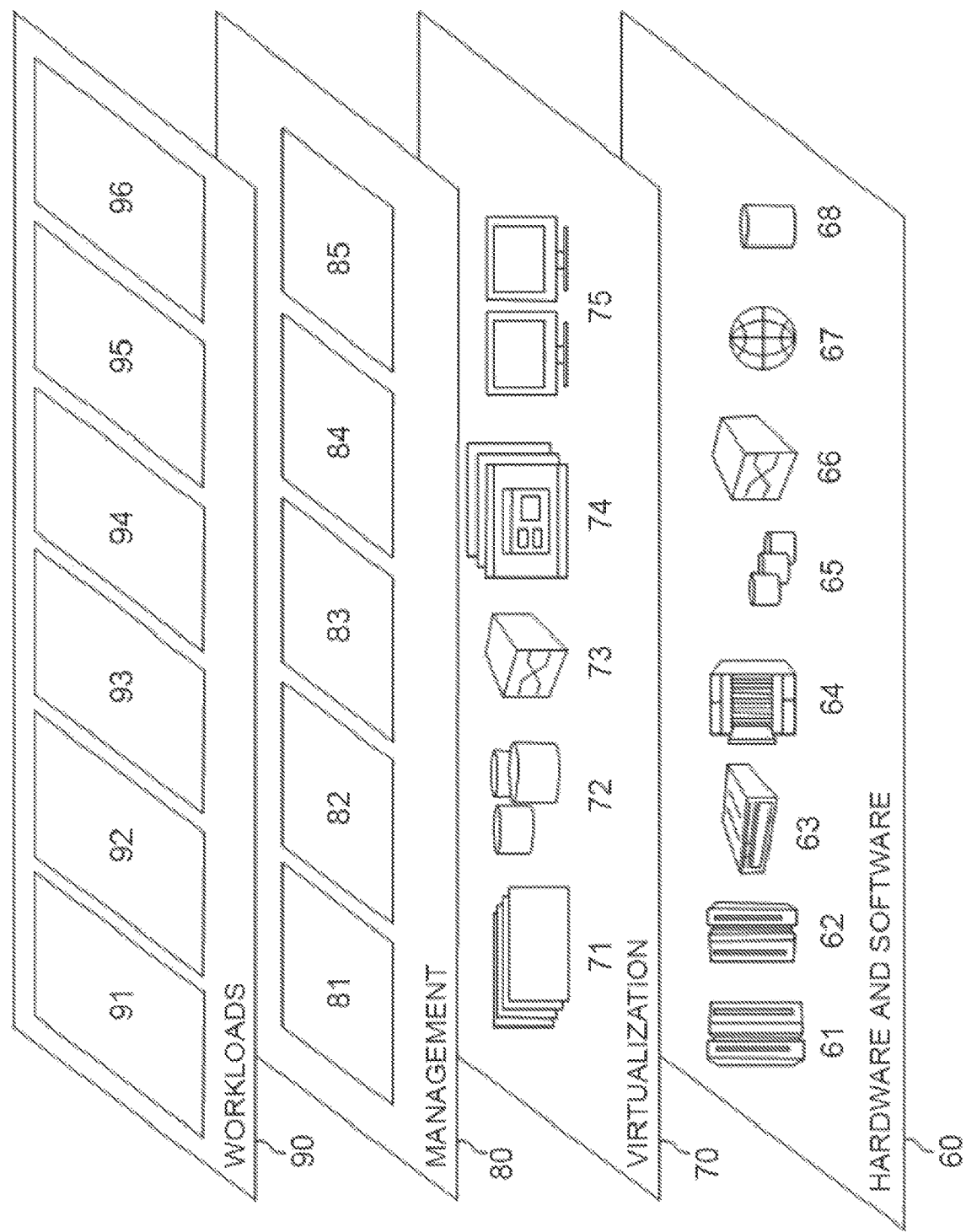
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing for dual-test assessment of operator cognitive or impairment state according to aspects of the present invention 96.

Figure 3:
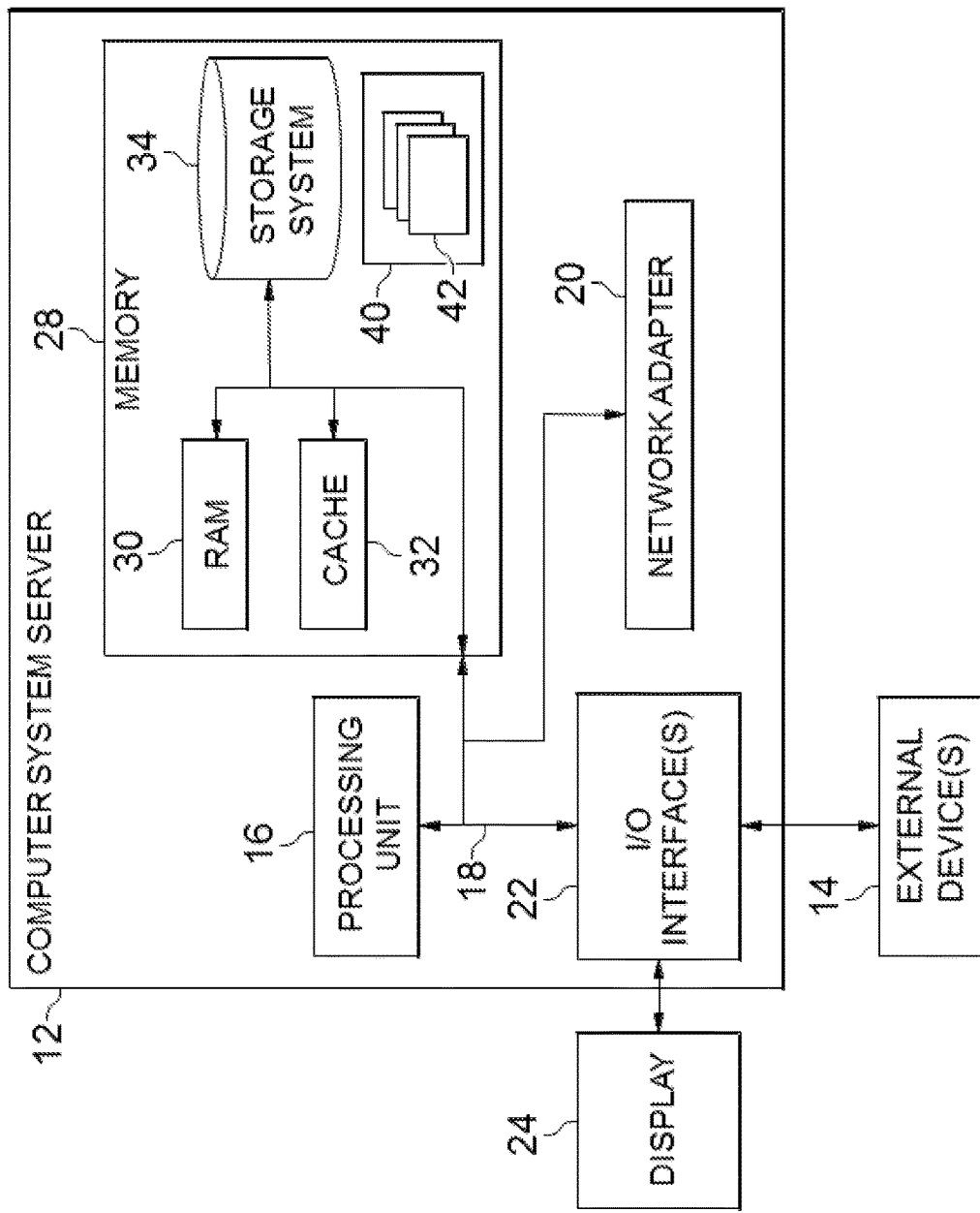
FIG. 3 depicts a computerized aspect according to an embodiment of the present invention.

FIG. 3 is a schematic of an example of a programmable device implementation 10 according to an aspect of the present invention, which may function as a cloud computing node within the cloud computing environment of FIG. 2. Programmable device implementation 10 is only one example of a suitable implementation and is not intended to suggest any limitation as to the scope of use or functionality of embodiments of the invention described herein. Regardless, programmable device implementation 10 is capable of being implemented and/or performing any of the functionality set forth hereinabove.

A computer system/server 12 is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

The computer system/server 12 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 4:
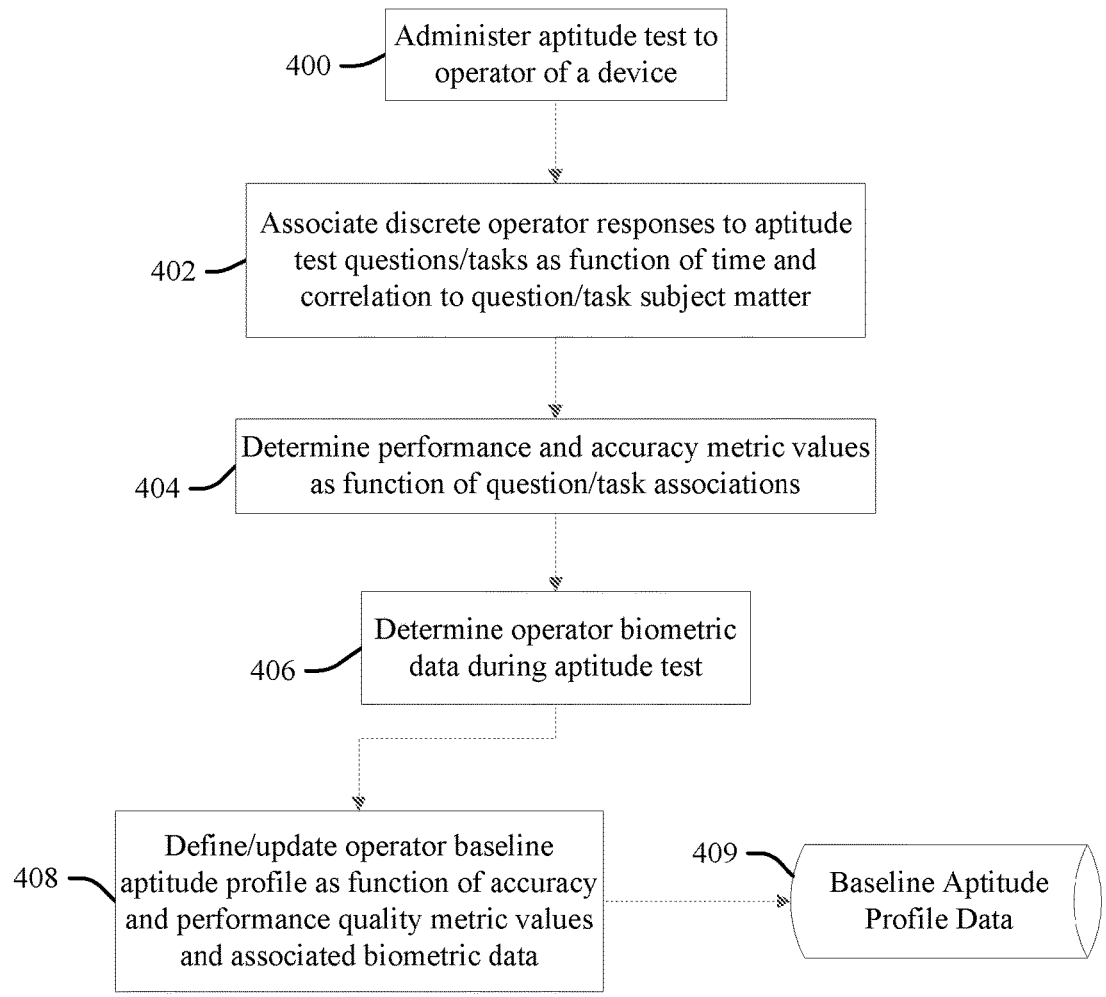
FIG. 4 is a block diagram illustration of an embodiment of the present invention.

FIG. 4 illustrates a system, process, or device according to an embodiment of the present invention. At 400 a processor that is configured according to the present invention (the "configured processor") administers an aptitude test to an operating user (an "operator") of a device, and in some embodiments while the operator is actively engaged in operating the device. Activities could include driving, using heavy machinery, playing an instrument or anything that can have a quality measurement. Illustrative but not exhaustive examples of the device include a an instrument or a component thereof, a diagnostic device, a mechanical or robotic apparatus, an automobile or other motorized vehicle, a boat, a crane, a forklift, a motorcycle, a saw or other power tool, a drawbridge, etc. Thus, actively engaged in operating the device includes driving an automobile, operating controls that direct movements of an instrument or component thereof, a power saw, a drawbridge, etc.

Embodiments may administer the aptitude test to the operator at 400 while the operator is actively engaged in operating the device: this is intended to better correlate performance of the operator assessed by the test to the cognitive assets available to the use of the operator while driving the operator is primarily engaged in operating the device (driving the vehicle, etc.), as the active engagement in operating the device demands primary attention and focus of the operator.

The aptitude test is configured to test cognitive and physical motion abilities of the operator that may not be directly related to performance in operating the device. Administering the aptitude test generally comprises driving audio speakers to present one or more audible content challenges (questions or task request descriptions) to the operator that comprise text content transformed into speech via text-to-speech processes, and wherein the text content asks the operator to provide an answer in satisfaction of a question, or to perform a physical movement or execute a mechanical evolution (for example, "turn a light switch on and off two times," "toot your horn twice," etc.).

At 402 the configured processor associates discrete responses from the operator to respective ones of the aptitude test challenges as a function of time and correlation to question or task subject matter. The responses are generally discrete portions of verbal speech data and/or physical movements (for example, stating the operator name or birth month, honking the horn, etc.). Association is a function of time, wherein the nearest-in-time responses are associated most strongly (given a highest association value or weighting) with respect to each question or task (as a most-likely response to that challenge, due to proximity in time). Association is also a function of strength of correlation to question or task subject matter: thus, a response of turning a specified light on and off is associated to a task requesting the action, or text content stating the middle name of the operator is associated to a question that asks for the middle name, even where the response is not most proximate in time to the task (for example, the operator honked a horn or stated her birth month prior to switching the light on and off, or stating her middle name).

At 404 the configured processor determines performance (speed, efficiency in response (amount of excess variable or pauses to think of answer, etc.) and accuracy and other performance quality metric values for each response as a function of the challenge associations at 402. Thus, some embodiments determine a degree of deviation from the value of the answer provided by the user to a cognitive test question as a function of a difference in an elapsed time between presenting the cognitive test question to the user and the answer provided by the user, relative to an average question response time defined for the user by the baseline aptitude profile data. Embodiment may also determine a percentage or amount of correlation of an answer to a correct response, including relative to a value defined within the baseline data for the user: for example, a 50% score for switching a light on and off once in response to a direction to perform the task twice, wherein the user usually (historically) complies and switches the light on and off twice; or a 67% score for providing month and date in response to a request for full birth date, due to omitting the required year; and responsive to directness (for example, an amount of extraneous sounds or unrelated text content interjected between a question and an appropriate, correct answer does not exceed average amounts of extraneous content defined by the baseline cognitive profile data).

Some embodiments further determine biometric data for the operator at 406 during administration of the aptitude test. Biometric data generally refers to body dimension and physical behavior measurement values and calculations, including those obtained from mobile, wearable and sensor-based devices used while in physical contact or in proximity to a user. Thus, embodiments may acquire physiological biometric data for the operator at 406 from sensor components that includes heartbeat, heartrate, respiration amounts or rates or constituent components, and blood components or levels (oxygen, caffeine, insulin, sugar, and alcohol or other intoxicants, stimulants, etc.). Biometric audio data may include sound profile data obtained by microphones from spoken responses to questions or tasks, including speech tone and volume and rate of speech. Biometric image data generated by user activities may be obtained from fitness trackers and other personal biometric sensors, as well as image data from cameras in the environment of the user; for example, from cameras internal to a smart phone, smart contact lens, eyeglass devices worn by a user or other person, etc.

At 408 the configured processor defines or updates a baseline aptitude profile data 409 for the operator as a function of the responses and their determined accuracy and performance quality metric values, in association to the aptitude test questions and tasks and associated biometric data. Thus, with each subsequent iteration of administering an aptitude test and assessing operator responses and biometric context at 400, 402, 404 and 406 and updating at 408 baseline scores within the operator profile data 409, embodiments train the baseline aptitude profile data 409, learning and increasing confidences in scores and patterns defined from the test performance metrics for use in comparison to subsequent answers and responses, against which future aptitude test scores and performances are compared in assessment of the operator, as discussed below.

Figure 5:
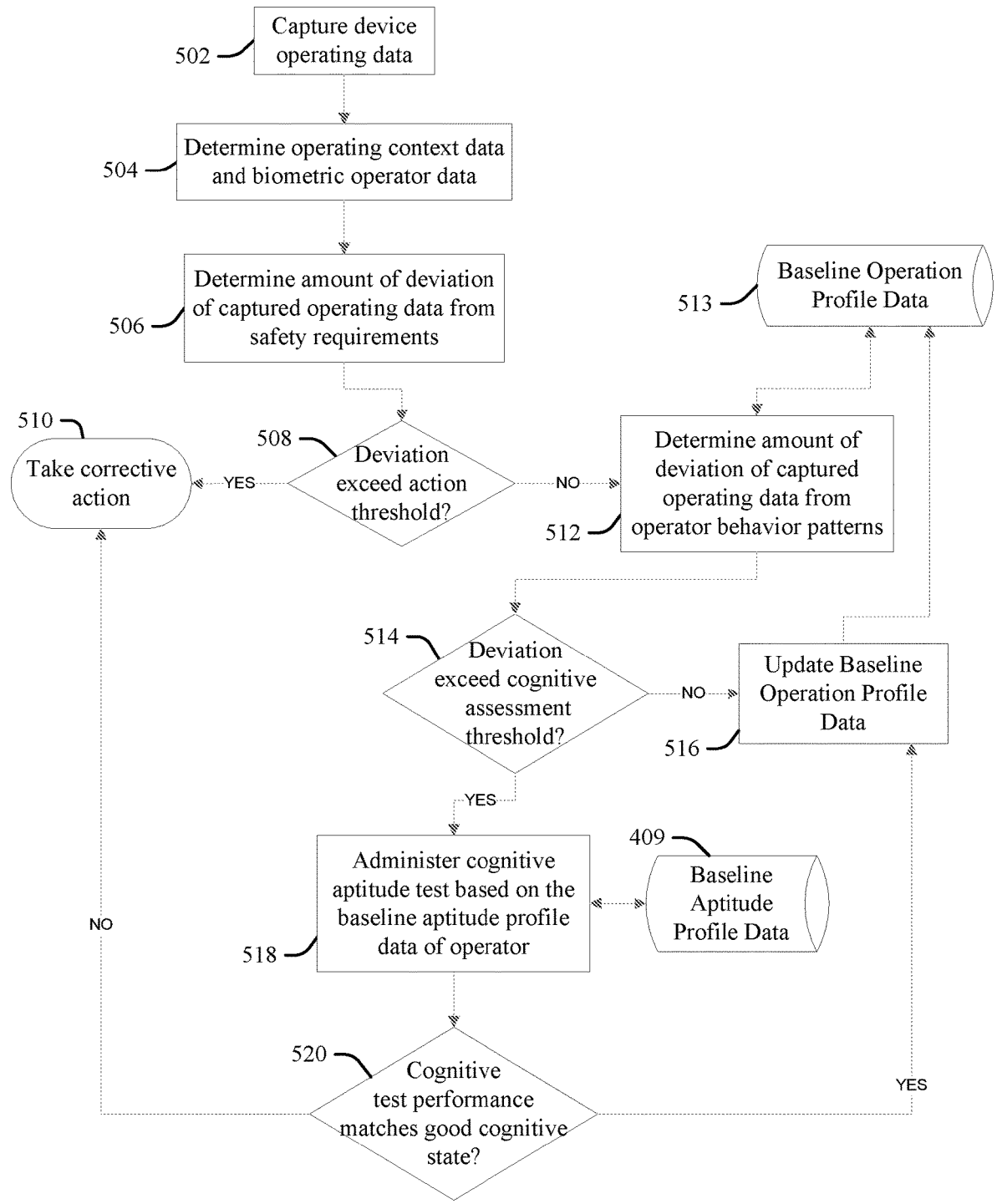
FIG. 5 is a block diagram illustration of another embodiment of the present invention.

Thus, referring now to FIG. 5, in response to identifying (at a time subsequent to a time of the training process described above with respect to FIG. 4) that the operator is operating a device (for example, starting up and driving a vehicle, operating a crane, manipulating an instrument, etc.), at 502 a processor that is configured according to the present invention (the "configured processor") captures operating data that is related to or indicative of the manner in which the operator is interacting with and guiding the movements ("operating") the device (for example, speed and direction of motion of the device in response to physical movements or voice commands from the operator, throttle and braking actions and steering inputs, etc.) Operating data may be gathered at 502 directly from device components (speedometers, tachometers, foot pedal and hand control inputs, etc.), as well as from operator cell phones or smart watches or components thereof or in communication therewith (cameras, biometric and environmental sensors, etc.) and other networked "Internet of Things" ("IOT") devices.

At 504 the configured processor determines operating context data inclusive of time (for example, time of day or night in hours, minutes and seconds, and calendar date indicia), place (geographic location data, inclusive of global positioning satellite (GPS) or cellular or radio telephony coordinates), weather conditions (for example, clear visibility, or rain, snow, fog, or cloudy conditions; temperature, humidity, dewpoint or other data or observations), light conditions of the operation (for example, in sunlight in clear conditions, or nighttime with no moonlight or natural illumination, etc.), and biometric operator data (for example, the biometric data listed and described above with respect to element 406 of FIG. 4).

At 506 the configured processor determines a degree of deviation of the monitored operation of the device from applicable safety requirements (laws, standards and regulations, etc.). For example, determining an amount or frequency that speed of motion exceeds applicable speed limits, including as modified by weather conditions under rules applicable to the operator (for example, an employer may require that vehicle speeds not exceed posted limits by more than five (5) miles-per-hour under normal conditions, and not more than the posted limit during snow or rain conditions). Embodiments may track movements to determine frequency or extent that the device deviates from travelling within designated lane markings to permissible limits, or compare following distances to applicable standards (for example, determine if or how often following distance is less than two (2) seconds in drive pavement conditions, or four (4) seconds in rain or snow conditions; or determine whether operator honks a warning horn a minimum two (2) times before driving a front end loader up a worksite hillside; still other examples will be apparent to one skilled in the art.

At 508 the configured processor determines whether the determined amount that the monitored operation deviates from the applicable safety requirements exceeds a corrective action threshold: more particularly, determining whether the deviation amount of the operation or operator behavior or biometric values requires immediate action to obviate an unsafe condition, wherein at 510 the configured processor automatically takes corrective action. For example, in response to determining at 508 that the amount that speed of motion exceeds applicable speed limits, reaches an unsafe margin threshold, or that the time of deviation from designated lane markings exceeds more than five (5) seconds, or occurs more often than a maximum allowable frequency of one deviation per five minutes, or the blood content monitors report a blood alcohol level above a legal limit, at 510 the configured processor takes a corrective action that initiates an "auto-shut-down" component that stops movement of the device in a safe fashion.

In other examples corrective action at 510 includes initiating an autonomous vehicle process that takes over control from the operator and directs the vehicle to continue travelling under autonomous control, including to reroute the vehicle to return to a "home" or safe, staging location so that the operator can rest or get medical attention (in response to biometric impairment indications). In some embodiments the corrective action 510 includes automatically stopping machinery operations, and preventing the operator from resuming activity until a set amount of time has passed (for example, to impose a statutorily-mandated rest period applicable to long-haul truckers), or until biometric data indicates that the operator is no longer impaired (has a safe blood alcohol level) or no longer fatigued or showing signs of illness, etc.

In response to determining that the corrective action threshold is not met at 508, at 512 the configured processor determines an amount that the determined operator performance or biometric values deviate from good performance pattern values defined (uniquely) for the operator within baseline operation profile data 513. More particularly, the baseline operation profile data 513 comprises normative, safe behavior patterns determined from historic operational, biometric and context data that are determined (labeled) to comprise good, safe operations (no accidents, no regulation infractions, safe, timely delivery of goods, etc.), by the same or analogous operators, defined by processing historic operating and biometric data from device components and the operator(s) via IOT devices, etc., during previous iterations or operation of the same (or analogous) device. In some embodiments the profile data is personal to each operator, wherein the operator is automatically identified at 512 and matched to unique baseline operation profile data for that operator as function of identifying indicia (for example, fingerprint or eye scanner profile data or other unique biometric data; unique employee identity numbers scanned from magnetic strips on key-fobs or identification cards, or broadcast therefrom via RFID mechanisms, and still other indicia will be apparent to one skilled in the art.)

For example, embodiments may define and train the baseline operation profile data 513 as a function of data observations associated to historically good performances of the operator, including speed observations, maneuvering consistency (for example, frequency of oversteering to correct wandering outside of a lane), historic frequency of sudden control adjustments (for example, abrupt braking and skidding), average operator heartrates and attentiveness values (for example, eye movement patterns, pupil dilation amounts relative to context lighting, patterns of directions of focus while operating the device. Data processed may include image data from cameras, wherein the embodiments determine whether the operator has stopped checking mirrors or blind spots thereof, is or is not actively moving his or her eyes to scan for obstruction issues, is changing lanes without signaling, swerving, tailgating, or showing signs of falling asleep, or even sleeping. Braking and acceleration patterns can also be checked, and still other data will be apparent to one skilled in the art.

At 514 the configured processor determines whether the amount that the determined operator performance or biometric values deviate from the good performance pattern values exceeds cognitive assessment threshold. If not, at 516 the configured processor updates (revises, learns additional values or patterns, etc.) values of the Baseline Operation Profile Data 513 as function of the current operator performance and/or biometric values.

Otherwise, if the deviation meets or exceeds the cognitive assessment threshold at 514, then at 518 the configured processor administers a cognitive aptitude test that comprises challenges (questions or requests) selected from or based on the baseline aptitude profile data 409 (as defined and discussed above with respect to FIG. 4). In one embodiment the test comprises straightforward and simple queries and task requests presented to the operator via audio, text-to-speech processes, requesting that the operator provide verbal answers to math problems, etc. (which is converted to text content via speech-to-text processes), or to physically manipulate a device component control object (for example, switch a light on and off, or activate a certain control knob), wherein the answers or responses do not require primary attention by the operator, but wherein the operator may continue to operate the device (drive a vehicle, etc.) without undue interference or competition for cognitive resources required to perform the test challenge. The aptitude test administered to the operator is configured to be similar but not necessarily identical to the aptitude test questions and tasks administered to establish baseline aptitude test scores (at 400, FIG. 4).

At 520 the configured processor determines whether the operator performance (answers and responses provided) in the cognitive test at 518 match (meet within an acceptable level of deviation) expected performance parameters that are associated with a good cognitive state. More particularly, the configured processor determines whether speed and/or accuracy metrics from the current test match values that are associated to good performances in previous cognitive testing in the Baseline Aptitude Profile Data 409, and therefore, likely to a good cognitive state. Statistically significant deviation from baseline cognitive aptitude score metrics may signal impairment. In one embodiment of the present invention, aptitude testing consists of audible questions which the operator answers verbally, wherein a delay in answering a question (relative to normative times for providing an answer as established in the baseline), or affectations in the operator's voice such as slurred speech or different tonalities, may indicate (in proportion to the amount of deviation from the baselines) a higher risk rating. For example, embodiments may determine that if the operator takes (significantly) longer to answer questions relative to the baseline testing, they may correspondingly more likely to be in an impaired state.

Embodiments provide testing and assessment processes that are uniquely tailored to the operator through iterative monitoring and baseline creation, wherein testing mechanisms are enabled to engage the operator in an efficient, audible, conversational cognitive testing process. By selecting questions or tasks appropriate to a particular operator, embodiments execute cognitive tests that are minimally distracting or demanding of attention from the operator, thereby enabling the operator to focus attention on safe operation of the device while the assessment test is executed.

By comparing operator activity data values to historic, normal ranges of operator baseline behavior data 513, some embodiments determine risk scores at 512 as a function of the deviation values that quantify an amount of likelihood of risk of loss or accident that is currently presented by operator by completing activities differently than normal, taking increased risks, presenting non-normal biometric data. In contrast, under the prior art no concerns would be recognized, and no risk values recognized or quantified, since the operator is otherwise operating within the minimum requirements of safety standards (as applied at 508).

Thus, embodiments of the present invention provide advantages in increasing safety by identifying deviations from normal behavior that, while not sufficient to trigger action under the prior art, are recognized as possibly indicative of impaired operational abilities by the operator (for example, due to fatigue, or an aggravated emotional state, or an onset of an acute medical condition that is as of yet asymptomatic), including where the operator is unaware that they are, in fact, in or progressing toward a compromised physical condition. Embodiments automatically and timely trigger administration of a cognitive test (at 518), and quickly assess the results (at 520) and take corrective action (at 510) as needed before the diminished state of the operator causes an accident.

Embodiments provide machine learning processes (at 408, FIG. 4, and at 516, FIG. 5) that define and train the baseline aptitude profile data (409) and the baseline operation profile data (513), autonomously learning and revising patterns of behavior, scores and confidence values and weights that define typical and atypical performance values for the operator in operating the device. Embodiments may also use iterative pattern monitoring to measure the operator movements and actions to continuously define and determine operator movement and response patterns relative to operation context in developing the operator's baseline profile data values.

Embodiments may select an appropriate corrective action at 510 as a function of the respective amounts of deviation from the baseline operation data 513 or the baseline cognitive aptitude data 409. For example, in response to determining that the deviations values compared at 508 and 514 do not greatly exceed the respective thresholds (for example, by less than 5% or some other criteria or margin that indicates a heightened concern or likelihood of risk of loss from the current cognitive state of the user), embodiments may select notification messaging as the corrective actions taken at 510, informing the operator that they are showing signs of fatigue or impairment, and suggesting a courses of action, (for example, "stop at your next opportunity and take a rest, or turn over the controls to the autonomous system"). In contrast, in response to determining that at least one of the deviations exceeds a respective threshold by a heightened concern margin (for example, by more than 15% or some other criteria of enhance concern margin), embodiments may activate a more immediate or drastic action, such as directly intervening into control over the device by the user (for example, taking over control of steering and movement or speed of the device, and/or initiating an immediate shut-down of the device.

Some variation in behavior or performance is transitory, or natural and fleeting. Accordingly, by continuously monitoring the operator and updating the baseline device operation profile data 513 at 516, embodiments of the present invention build and learn a personalized database of behavior that is unique to each operator, and enable the embodiments to better distinguish unique behaviors of the operator that are merely quirks, from deviations from norms that present risk of accident and loss. For example, two different operators with equivalent, good safety records may have different habits in operating the same piece of heavy machinery: by matching the performance of either to their own personal history, embodiments are less likely to (falsely) determined that the operations of one is more risky than the other, merely due to differences in comparison to generic norms, as is the case in the prior art. Instead, using data specific to each operator that is processed and stored to build a personalized baseline of habits from which the invention determines impairment, embodiments define thresholds for triggering impairment determinations that are different for each operator, based on different, personal habits and unique behaviors, and are therefore more accurate in identifying and predicting deviations within individual operator behaviors that should trigger concern, and corrective actions before accidents and losses occur.

When people are completing activities differently than they normally do, including taking increased risks, there is a possibility that such behaviors indicate the presence of an impaired state that may diminish their cognitive abilities and overall information processing abilities, resulting in corresponding diminishment in their abilities to recognize and obviate risky situations (for example, to react proactively to an onset of bad weather and begin to slow down in time in order to avoid skidding into vehicles coming to a stop in front of their vehicle). Different operators may have different speed or maneuvering option selection habits and tendencies, including in different weather conditions. Aspects of the present invention use the combination of two test processes to determine when a given deviation from a typical operation pattern is in fact an indication of concern (when it is confirmed by a combination with a separate, cognitive operation deviation determination value), rather than just a personal quirk or transitive anomaly with respect to the operator that does not trigger the need to take corrective action. If a driver is not as focused as normal (as confirmed by the cognitive test result deviation value), and is driving with increased risks over his/her normal pattern, aspects of the present invention autonomously identify the risk and promptly take appropriate corrective actions.

The terminology used herein is for describing aspects only and is not intended to be limiting of the invention. As used herein, singular forms "a", "an", and "the" are intended to include the plural forms as well, unless the context clearly indicates otherwise. It will be further understood that the terms "include" and "including" when used in the specification specify the presence of stated features, integers, steps, operations, elements, and/or groups thereof. Certain examples and elements described in the present specification, including in the claims, and as illustrated in the figures, may be distinguished, or otherwise identified from others by unique adjectives (e.g. a "first" element distinguished from a "second" or "third" of a plurality of elements, a "primary" distinguished from a "secondary" one or "another" item, etc.) Such identifying adjectives are generally used to reduce confusion or uncertainty and are not to be construed to limit the claims to any specific illustrated element or embodiment, or to imply and precedence, ordering, or ranking of any certain elements, limitations, or process steps.

The descriptions of the various embodiments of the present invention have been presented for the purposes of illustration but are not intended to be exhaustive or limited to the embodiments disclosed. Many modifications and variations will be apparent to those of ordinary skill in the art without departing for the scope and spirit of the described embodiments. The terminology used herein was chosen to best explain the principles of the embodiments, the practical applications or technical improvement over technologies found in the marketplace, or to enable others of ordinary skill in the art to understand the embodiments disclosed herein.

What is claimed is:

1. A computer-implemented method, comprising:
    in response to determining that performance data of operation of a device by an operating user meets a safety requirement, determining a degree of deviation of a value of the performance data from a baseline pattern of good performance values defined for the user;
    in response to determining that the degree of deviation of the operating data value meets a cognitive assessment threshold, administering a cognitive aptitude test to the user that comprises a cognitive test challenge that is selected from baseline aptitude profile data that comprises challenges previously responded to by the user; and
    in response to determining that a degree of deviation of a value of a response provided by the user to the cognitive test challenge from a performance metric value of the baseline aptitude profile data meets a threshold cognitive assessment threshold, executing a corrective action that reduces a risk of loss from impaired cognitive performance in the operation of the device by the user.

2. The method of claim 1, wherein the administering the cognitive aptitude challenge comprises presenting audible content of the challenge to the user via an audio speaker while the user is operating the device, and wherein the audible content is selected from the group consisting of a cognitive test question, and a request to physically manipulate a device component control object.

3. The method of claim 2, further comprising:
    determining the degree of deviation of the value of the response provided by the user to the cognitive test challenge as a function of a difference in an elapsed time between a time of the presenting the cognitive test challenge audible content to the user and a time of the response provided by the user, and an average challenge response time defined for the user by the baseline aptitude profile data.

4. The method of claim 3, further comprising:
    determining the degree of deviation of the value of the response provided by the user to the cognitive test challenge as a function of a percentage of correlation of the answer content to an average answer content amount defined for the user by the baseline cognitive profile data.

5. The method of claim 1, further comprising:
    training values of the baseline operation profile data as a function of data observations associated to historically good performance of the user while operating the device.

6. The method of claim 1, further comprising:
    in response to determining that the degree of deviation of the value of the response provided by the user to the cognitive test challenge from the performance metric value of the baseline aptitude profile data does not exceed the threshold cognitive assessment threshold by more than a heightened concern margin value, executing the corrective action by providing a notification to the user that the user is likely in a cognitively impaired state; and
    in response to determining that the degree of deviation of the value of the response provided by the user to the cognitive test challenge from the performance metric value of the baseline aptitude profile data exceeds the threshold cognitive assessment threshold by more than the heightened concern margin value, executing the corrective action by directly intervening into control over the device by the user.

7. The method of claim 1, further comprising:
    integrating computer-readable program code into a computer system comprising a processor, a computer readable memory in circuit communication with the processor, and a computer readable storage medium in circuit communication with the processor; and
    wherein the processor executes program code instructions stored on the computer-readable storage medium via the computer readable memory and thereby performs the determining the degree of deviation of the value of the performance data from the baseline pattern of good performance values defined for the user, the administering the cognitive aptitude test to the user, and the executing the corrective action.

8. The method of claim 7, wherein the computer-readable program code is provided as a service in a cloud environment.

9. A computer system, comprising:
    a processor;
    a computer readable memory in circuit communication with the processor; and a computer readable storage medium in circuit communication with the processor;

wherein the processor executes program instructions stored on the computer-readable storage medium via the computer readable memory and thereby:

in response to determining that performance data of operation of a device by an operating user meets a safety requirement, determines a degree of deviation of a value of the performance data from a baseline pattern of good performance values defined for the user;

in response to determining that the degree of deviation of the operating data value meets a cognitive assessment threshold, administers a cognitive aptitude test to the user that comprises a cognitive test challenge that is selected from baseline aptitude profile data that comprises challenges previously responded to by the user; and in response to determining that a degree of deviation of a value of a response provided by the user to the cognitive test challenge from a performance metric value of the baseline aptitude profile data meets a threshold cognitive assessment threshold, executes a corrective action that reduces a risk of loss from impaired cognitive performance in the operation of the device by the user.

10. The system of claim 9, wherein the processor executes the program instructions stored on the computer-readable storage medium via the computer readable memory and thereby administers the cognitive aptitude challenge by presenting audible content of the challenge to the user via an audio speaker while the user is operating the device; and wherein the audible content is selected from the group consisting of a cognitive test question, and a request to physically manipulate a device component control object.

11. The system of claim 10, wherein the processor executes the program instructions stored on the computer-readable storage medium via the computer readable memory and thereby determines the degree of deviation of the value of the response provided by the user to the cognitive test challenge as a function of a difference in an elapsed time between a time of the presenting the cognitive test challenge audible content to the user and a time of the response provided by the user, and an average challenge response time defined for the user by the baseline aptitude profile data.

12. The system of claim 11, wherein the processor executes the program instructions stored on the computer-readable storage medium via the computer readable memory and thereby determines the degree of deviation of the value of the response provided by the user to the cognitive test challenge as a function of a percentage of correlation of the answer content to an average answer content amount defined for the user by the baseline cognitive profile data.

13. The system of claim 9, wherein the processor executes the program instructions stored on the computer-readable storage medium via the computer readable memory and thereby:

train values of the baseline operation profile data as a function of data observations associated to historically good performance of the user while operating the device.

14. The system of claim 9, wherein the processor executes the program instructions stored on the computer-readable storage medium via the computer readable memory and thereby:

in response to determining that the degree of deviation of the value of the response provided by the user to the cognitive test challenge from the performance metric value of the baseline aptitude profile data does not exceed the threshold cognitive assessment threshold by more than a heightened concern margin value, executes the corrective action by providing a notification to the user that the user is likely in a cognitively impaired state; and in response to determining that the degree of deviation of the value of the response provided by the user to the cognitive test challenge from the performance metric value of the baseline aptitude profile data exceeds the threshold cognitive assessment threshold by more than the heightened concern margin value, executes the corrective action by directly intervening into control over the device by the user.

15. A computer program product, comprising:

a computer readable storage medium having computer readable program code embodied therewith, the computer readable program code comprising instructions for execution by a processor that cause the processor to:

in response to determining that performance data of operation of a device by an operating user meets a safety requirement, determine a degree of deviation of a value of the performance data from a baseline pattern of good performance values defined for the user;

in response to determining that the degree of deviation of the operating data value meets a cognitive assessment threshold, administer a cognitive aptitude test to the user that comprises a cognitive test challenge that is selected from baseline aptitude profile data that comprises challenges previously responded to by the user; and in response to determining that a degree of deviation of a value of a response provided by the user to the cognitive test challenge from a performance metric value of the baseline aptitude profile data meets a threshold cognitive assessment threshold, execute a corrective action that reduces a risk of loss from impaired cognitive performance in the operation of the device by the user.

16. The computer program product of claim 15, wherein the computer readable program code instructions for execution by the processor further cause the processor to administer the cognitive aptitude challenge by presenting audible content of the challenge to the user via an audio speaker while the user is operating the device; and wherein the audible content is selected from the group consisting of a cognitive test question, and a request to physically manipulate a device component control object.

17. The computer program product of claim 16, wherein the computer readable program code instructions for execution by the processor further cause the processor to determine the degree of deviation of the value of the response provided by the user to the cognitive test challenge as a function of a difference in an elapsed time between a time of the presenting the cognitive test challenge audible content to the user and a time of the response provided by the user, and an average challenge response time defined for the user by the baseline aptitude profile data.

18. The computer program product of claim 17, wherein the computer readable program code instructions for execution by the processor further cause the processor to determine the degree of deviation of the value of the response provided by the user to the cognitive test challenge as a function of a percentage of correlation of the answer content to an average answer content amount defined for the user by the baseline cognitive profile data.

19. The computer program product of claim 15, wherein the computer readable program code instructions for execution by the processor further cause the processor to:
- train values of the baseline operation profile data as a function of data observations associated to historically good performance of the user while operating the device.

20. The computer program product of claim 15, wherein the computer readable program code instructions for execution by the processor further cause the processor to:
- in response to determining that the degree of deviation of the value of the response provided by the user to the cognitive test challenge from the performance metric value of the baseline aptitude profile data does not exceed the threshold cognitive assessment threshold by more than a heightened concern margin value, execute the corrective action by providing a notification to the user that the user is likely in a cognitively impaired state; and
- in response to determining that the degree of deviation of the value of the response provided by the user to the cognitive test challenge from the performance metric value of the baseline aptitude profile data exceeds the threshold cognitive assessment threshold by more than the heightened concern margin value, execute the corrective action by directly intervening into control over the device by the user.

* * * * *